United States Patent [19]
Einhorn et al.

[11] Patent Number: 5,279,304
[45] Date of Patent: Jan. 18, 1994

[54] NASAL VOLUME METER

[75] Inventors: Robert K. Einhorn, 138 Amity St., Apt. 1B, Brooklyn, N.Y. 11201; Istvan Szoke, 135 Willow St., Apt. 312, Brooklyn, N.Y. 11201; Jerzy Einhorn, 415 Summit Dr., Pittsburgh, Pa. 15228; Yosef P. Krespi, 1441 3rd Ave., New York, N.Y. 10028

[73] Assignees: Robert K. Einhorn, Brooklyn, N.Y.; Jerzy Einhorn, Pittsburgh, Pa.; Yosef P. Krespi, New York, N.Y.; Ansel M. Schwartz, Pittsburgh, Pa.

[21] Appl. No.: 876,510

[22] Filed: Apr. 30, 1992

[51] Int. Cl.$^5$ .............................. A61B 5/091
[52] U.S. Cl. ................... 128/724; 128/725
[58] Field of Search ................... 128/724, 725

[56]         References Cited
        U.S. PATENT DOCUMENTS

| | | | |
|---|---|---|---|
| 2,831,181 | 4/1958 | Warner | 128/724 |
| 3,687,130 | 8/1972 | McCormick | 128/724 |
| 3,903,875 | 9/1975 | Hughes | 128/724 |
| 3,962,917 | 6/1976 | Terada | 128/724 |
| 3,999,537 | 12/1976 | Noiles | 128/724 |
| 4,995,400 | 2/1991 | Boehringer et al. | 128/725 |

FOREIGN PATENT DOCUMENTS 197712 12/1977 U.S.S.R. .................. 128/724

OTHER PUBLICATIONS

Graystone, "A Self-Centering . . . Research", IEEE Trans on Bio-Med Eng., Sep. 1971, vol. BMEB-18, No. 5, pp. 382-383.
NASA Tech. Brief, 68-10438, Dec. 1968.

*Primary Examiner*—Lee S. Cohen
*Attorney, Agent, or Firm*—Ansel M. Schwartz

[57]         ABSTRACT

The present invention pertains to an apparatus for measuring nasal air flow. The apparatus includes a head for interacting with at least one of the nasal cavities of a patient. The head has a measuring chamber through which air is inhaled into and exhaled from the nasal cavity. A resistance wire is positioned within the measuring chamber with the path of air flow. There is also a current generator electrically connected to the resistance wire for providing a constant current through the resistance wire such that the resistance wire is heated. The apparatus further includes means for analyzing change in voltage across the resistance wire over time such that air flow through the measuring chamber is determined. The analyzing means is electrically connected to the resistance wire. There are also means for displaying the determined air flow. The present invention is also a method for measuring nasal air flow. The method comprises the first step of orienting a heated resistance wire in the air flow of a nasal cavity. Then, there is the step of analyzing the change in voltage over time across the resistance wire such that the amount of air flow past the resistance wire is determined. Preferably, after the analyzing step, there is the step of displaying the determined air flow. The displaying step can include the step of printing the determined air flow.

12 Claims, 3 Drawing Sheets

NASAL VOLUME METER

FIELD OF THE INVENTION

The present invention is related in general to medical measuring devices. More specifically, the present invention is related to a device for measuring nasal air flow.

BACKGROUND OF THE INVENTION

A number of intranasal pathological conditions, such as deviated septum, polyps, hypertrophic turbinates and spurs, trauma, choanal atresia, congenital problems or any infections such as sinitis require a device that can record intranasal status of the patient.

Rhinometry, nasal peak flow measure, and metal breathing plates are currently used to determine the intranasal status of a patient. Unfortunately, these methods are limited in value in the pre-operative evaluation of the nature and localization of an abnormality in the nasal cavity.

Imaging method such as computed tomography and magnetic resonance imaging are too expensive for routine use and do not add information about mucosal changes.

Acoustic rhinometry is used to evaluate the dimension of the nasal cavity by estimating the cross sectional area of the nasal cavity as a function of the distance from the nostril. Unfortunately, the equipment for acoustic rhinometry is quite cumbersome and not easily accessible to the average practicing physician.

The present invention provides a nasal flow meter which is of simple construction and can be used to show nasal flow analytically rather than symptomatically.

SUMMARY OF THE INVENTION

The present invention pertains to an apparatus for measuring nasal air flow. The apparatus includes a head for interacting with at least one of the nasal cavities of a patient. The head has a measuring chamber through which air is inhaled into and exhaled from the nasal cavity. A resistance wire is positioned within the measuring chamber with the path of air flow. There is also a current generator electrically connected to the resistance wire for providing a constant current through the resistance wire such that the resistance wire is heated. The apparatus further includes means for analyzing change in voltage across the resistance wire over time such that air flow through the measuring chamber is determined. The analyzing means is electrically connected to the resistance wire. There are also means for displaying the determined air flow.

The present invention is also a method for measuring nasal air flow. The method comprises the first step of orienting a heated resistance wire in the air flow of a nasal cavity. Then, there is the step of analyzing the change in voltage over time across the resistance wire such that the amount of air flow past the resistance wire is determined. Preferably, after the analyzing step, there is the step of displaying the determined air flow. The displaying step can include the step of printing the determined air flow.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
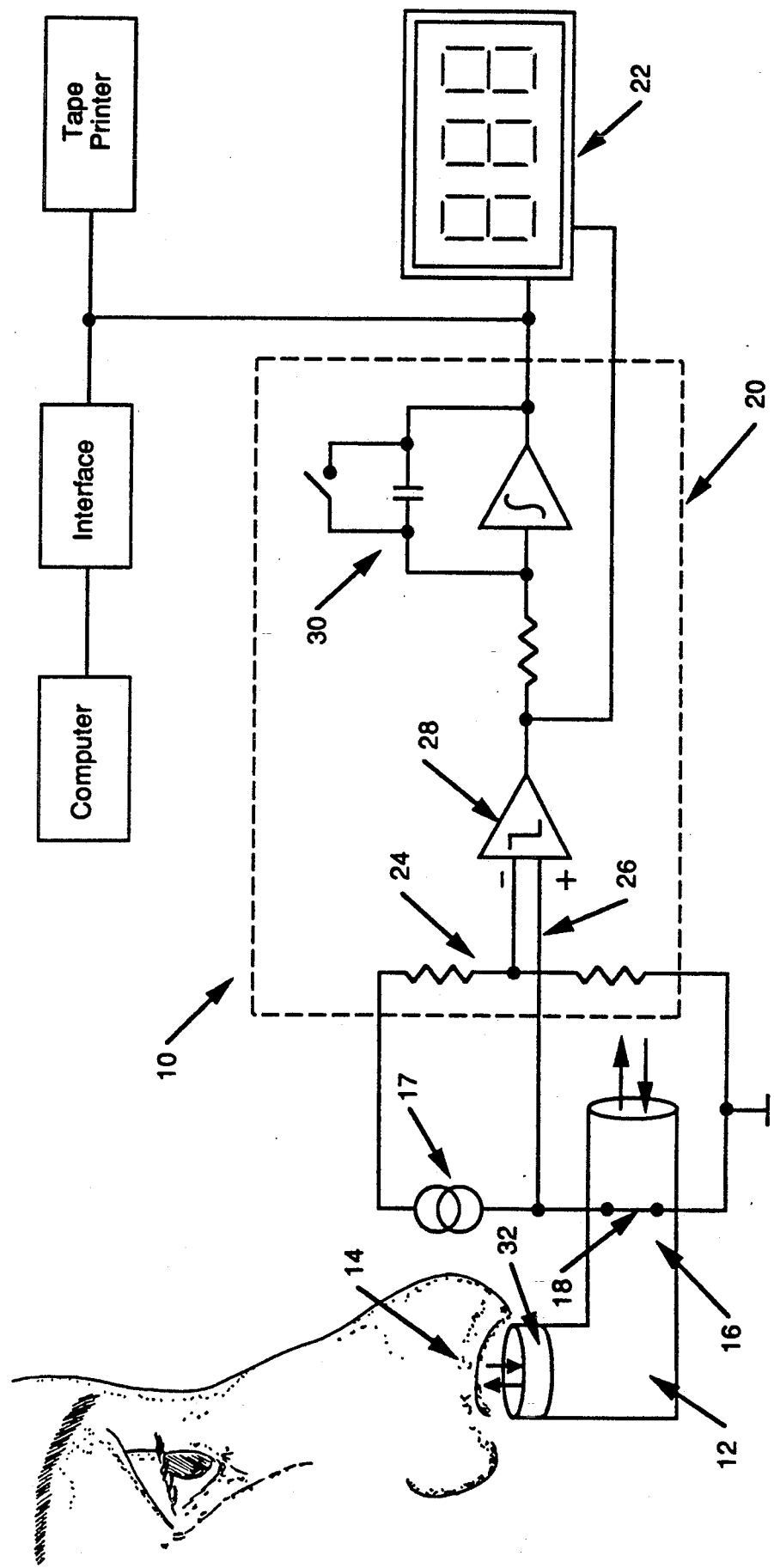
FIG. 1 is a schematic representation showing the apparatus for measuring nasal air flow.
Figure 2:
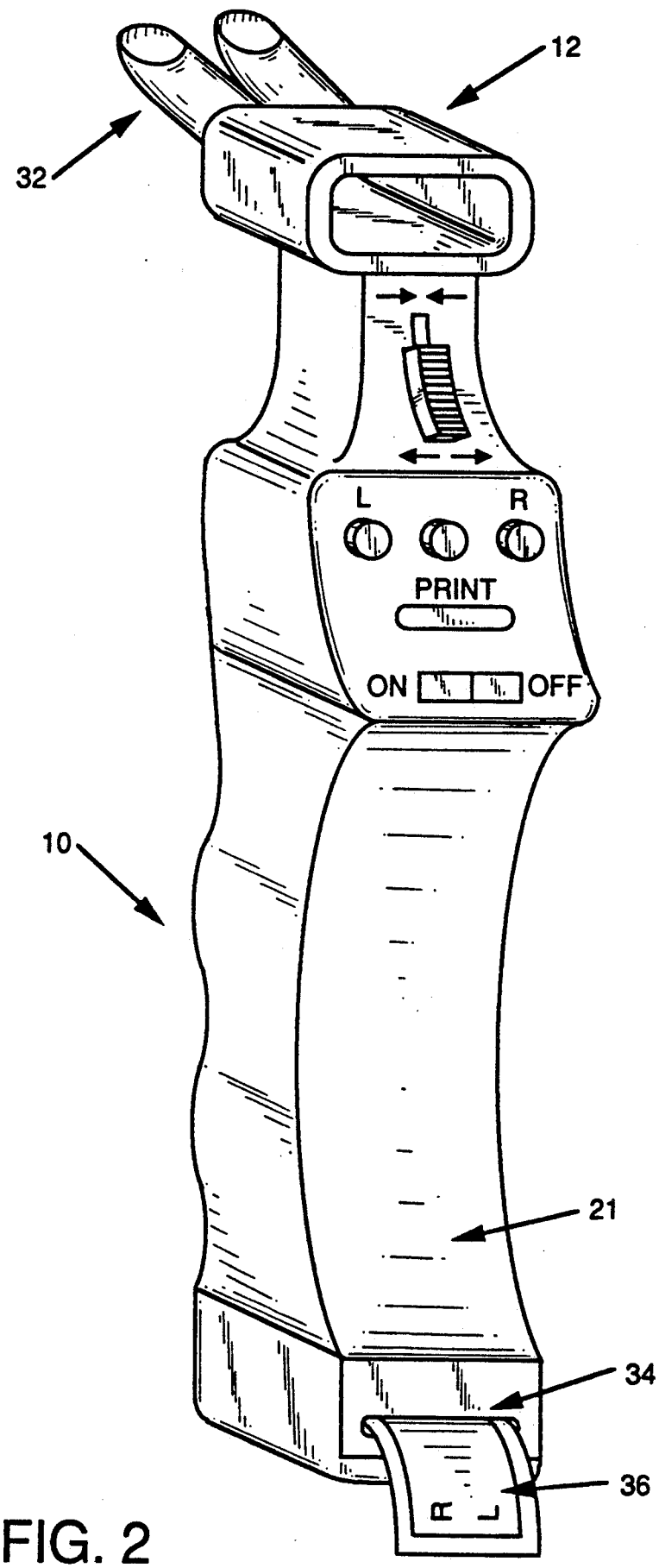
FIG. 2 is a schematic representation showing a perspective view of the apparatus.
Figure 3:
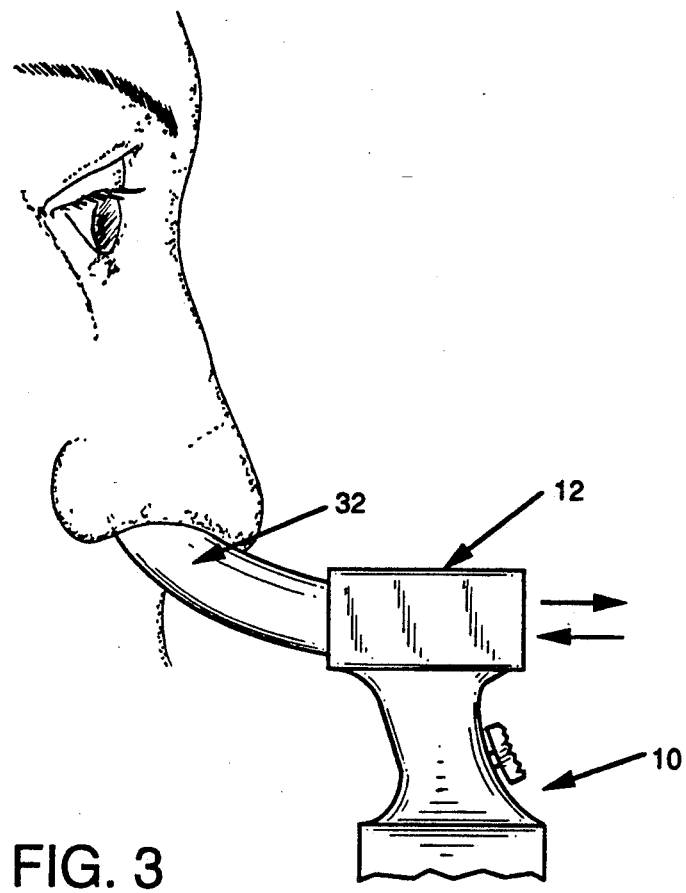
FIG. 3 is a schematic representation showing the apparatus in engagement with a patient's nasal cavity.
Figure 4:
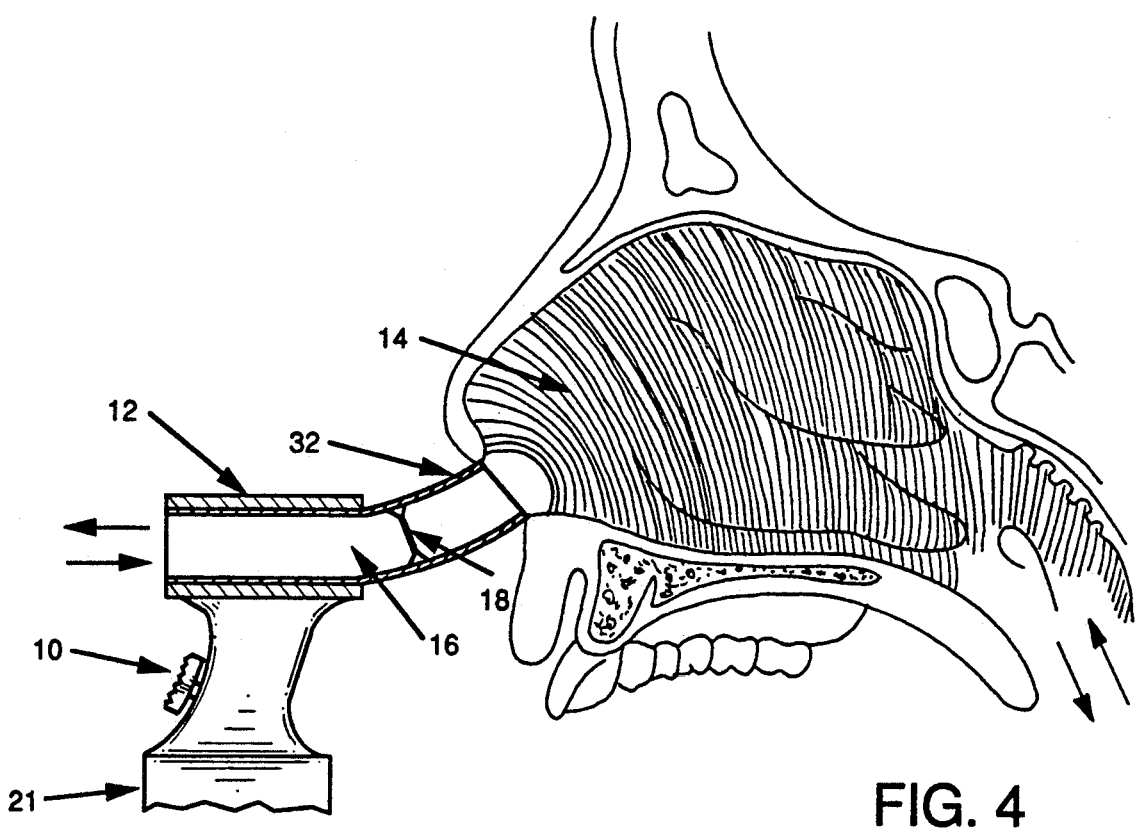
FIG. 4 is a schematic representation showing a cross sectional view of the apparatus in engagement with a patient's nasal cavity.

Referring now to the drawings wherein like reference numerals refer to similar or identical parts throughout the several views, and more specifically to FIGS. 1–4 thereof, there is shown an apparatus 10 for measuring nasal air flow. The apparatus 10 includes a head 12 for interacting with at least one of the nasal cavities 14 of a patient. The head 12 has a measuring chamber 16 through which air is inhaled into and exhaled from the nasal cavity 14. A resistance wire 18 is positioned within the measuring chamber 16 with the path of air flow. There is also a current generator 17 electrically connected to the resistance wire 18 for providing a constant current through the resistance wire 18 such that the resistance wire 18 is heated. The apparatus 10 further includes means 20 for analyzing change in voltage across the resistance wire 18 over time such that air flow through the measuring chamber 16 is determined. There are also means 22 for displaying the determined air flow, such as a digital volt meter which is built into the handle 21 of the apparatus.

The present invention is also a method for measuring nasal air flow. The method comprises the first step of orienting a heated resistance wire in the air flow of a nasal cavity. Then, there is the step of analyzing the change in voltage over time across the resistance wire such that the amount of air flow past the resistance wire is determined. Preferably, after the analyzing step, there is the step of displaying the determined air flow. The displaying step can include the step of printing the determined air flow.

In a preferred embodiment, the analyzing means includes a balanced bridge circuit 24. The balanced bridge circuit 24 has an output 26 which represents the voltage change across the resistance wire relative to the voltage across the resistance wire at zero air flow. The balanced bridge circuit 24 is connected to a voltage trigger circuit 28 which triggers when a voltage change occurs. The voltage trigger circuit 28 is connected to a proportional integrator 30 which generates a voltage which is proportional to the output voltage from the balanced bridge circuit 24 and the time passed since the trigger circuit 28 triggered. The proportional integrator 30 in turn is connected to a digital voltage meter which displays the air flow in convenient units of volume, such as cubic centimeters. The display means can also include a tape printer 34 which prints the measured air flow onto adhesive labels 36 which can be directly affixed to the patient's medical chart. The apparatus 10 can also include an interface for allowing the apparatus 10 to communicate with a computer. Preferably, the microalarspeculum 32, which is the part of the head 12 which contacts the patient, is disposable or at least sterilizable.

In the operation of the preferred embodiment, a disposable microalarspeculum 32 is connected to the head 12 of the apparatus 10. The head 12 is then pressed against one of the nasal openings of a patient. The mouth and other nasal opening are held closed during measuring so that the entire volume of air inhaled passes through the measuring chamber 16. The apparatus 10 is turned on which heats the resistance wire 18, which is platinum, to a temperature of 400° F with the current generator 17. The current generator maintains a constant current (I) across the resistance wire 18 regardless of its resistance. Once the head 12 of the apparatus 10 is interfaced with a nasal cavity 14 of the patient in a sealed relationship, the patient inhales and exhales. The subsequent air flow through the air chamber 16 acts to cool the heated resistance wire 18. It is a physical property of any metallic material that resistance to electrical current is dependent on temperature. Accordingly, the drop in temperature of the resistance wire 18 changes its resistance in proportion. The resulting resistance change changes the voltage proportionally across resistance wire 18 a proportional amount, since the current the generator 17 keeps the current steady (V=IR). This voltage change appears on the output 26 of the balanced bridge circuit 24. The proportional integrator 30 generates a voltage which is proportional to the voltage at the output 26 and the time passed since the trigger circuit 28 is triggered. A digital volt meter displays the voltage calculated by the proportional integrator in the appropriate units of volume. If it is desired, a tape printer 34 built into the handle 21 of the apparatus can print the measured volume on an adhesive label 36. The adhesive label 36 is then affixed to the medical chart of the patient for convenient reference. The measured air flow volume can also be sent to a computer for storage and further data manipulation. To ensure accuracy, the apparatus 10 is calibrated with a reference flow meter.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for measuring nasal air flow comprising:
   a head for interfacing with at least one of the nasal cavities of a patient in a sealed relationship such that essentially all of the air passing through the nasal passage flows through the head, said head having a measuring chamber through which air is inhaled and exhaled from the nasal cavity;
   a resistance wire disposed within the measuring chamber about which the air flows past;
   a current generator electrically connected to the resistance wire for providing a constant current through the resistance wire which heats the resistance wire;
   means for analyzing change in voltage across the resistance wire over time such that air flow through said measuring chamber is determined, said analyzing means in electrical communication with said resistance wire; and
   means for displaying said determined air flow, said displaying means in communication with said analyzing means.

2. An apparatus as described in claim 1 wherein the analyzing means includes a balanced bridge circuit electrically connected to the resistance wire having an output which represents the voltage change across the resistance wire relative tot he voltage across the resistance wire at zero air flow.

3. An apparatus as described in claim 2 wherein the analyzing means includes a voltage trigger CKT and a proportional integrator electrically connected to the output of the balanced bridge circuit.

4. An apparatus as described in claim 3 wherein the display means includes a digital volt meter electrically connected to the proportional integrator.

5. An apparatus as described in claim 4 wherein the display means includes a tape printer which records the determined air flow on adhesive labels.

6. An apparatus as described in claim 5 including an interface for communication with a computer, said interface in electrical communication with said analyzing means.

7. An apparatus as described in claim 6 wherein the resistance wire in comprised of platinum.

8. An apparatus as described in claim 5 including a hand-held housing attached to the head, said housing containing the current generator, the analyzing means, the displaying means and the tape printer.

9. An apparatus as described in claim 1 wherein the head includes a disposable microalarspeculum.

10. A method of measuring nasal air flow comprising the steps of:
    disposing ahead having a measuring chamber in a sealed relationship against a nasal cavity of a patient such that essentially all of the air passing through the nasal passage flows through the measuring chamber; and
    analyzing a change in voltage over time across a resistance wire in the measuring chamber such that the amount of air flow through the nasal cavity is determined.

11. A method as described in claim 10 wherein after the analyzing step, there is the step of displaying the determined air flow.

12. A method as described in claim 11 wherein the displaying step includes the step of printing the determined air flow.

* * * * *